(12) United States Patent
Park et al.

(10) Patent No.: US 7,264,791 B2
(45) Date of Patent: Sep. 4, 2007

(54) METHOD FOR PREPARING TECHNETIUM-LABELED ANTIMONY SULFIDE NANOCOLLOID

(75) Inventors: Sang Hyun Park, Daejeon-si (KR); Kyung Bae Park, Daejeon-si (KR); Byung Chul Shin, Daejeon-si (KR)

(73) Assignee: Korea Atomic Energy Research Institute (KR)

( * ) Notice: Subject to any disclaimer, the term of this patent is extended or adjusted under 35 U.S.C. 154(b) by 106 days.

(21) Appl. No.: 11/065,524

(22) Filed: Feb. 23, 2005

(65) Prior Publication Data

US 2005/0186134 A1    Aug. 25, 2005

(30) Foreign Application Priority Data

Feb. 24, 2004   (KR) ..................... 10-2004-0012394

(51) Int. Cl.
*A61K 51/00* (2006.01)
(52) U.S. Cl. ..................... 424/1.29; 424/489
(58) Field of Classification Search ............. 424/1.29
See application file for complete search history.

(56) References Cited

OTHER PUBLICATIONS

Park, Sang Hyun et al., "A facile and novel route to 99mTc-labeled antimony sulfide nancolloid," Chemistry Letters, vol. 33, No. 4, pp. 380-381, published on the web on Mar. 1, 2004.*
An article entitled "The Labeling of Nanocoll with . . . ", By Mitterhauser et al., published by Applied Radiation and Isotopes, vol. 59, (2003), pp. 337-342.
An article entitled "Deposition of Small 99mTc-Labelled Colloids in . . . ", By Nagai et al., published by European Journal of Nuclear Medicine, vol. 7, (1982), pp. 66-70.
An article entitled "Sentinel Node Metastasis in the Groin Detected by . . . ", By Haupsy et al., published by Gynecologic Oncology, vol. 86, (2002), pp. 358-360.
An article entitled "Sentinel Node Biopsy in 70 Unselected . . . ", By van der Ent et al., published by European Journal of Surgical Oncology, vol. 25, (1999), pp. 24-29.
An article entitled "Synthesis of Nir-Sensitive Au-Au2S . . . ", By Ren et al., published by Materials Science and Engineering, vol. 23, (2003), pp. 113-116.
An article entitled "Potential Technetium Small . . . ", By Jurisson et al., published by Chem. Rev., vol. 99, (1999), pp. 2205-2218.
An article entitled "Therapeutic Radiopharmaceuticals", By Volkert et al., published by Chem. Rev., vol. 99, (1999), pp. 2269-2292.
An article entitled "Studies on the Preparation of . . . ", By Park et al., published by The Korean Journal of Nuclear Medicine, vol. 23, (1989), pp. 71-83.
An article entitled "Preparation and Radiolabeling of . . . ", By Lin et al., published by Applied Radiation and Isotopes, vol. 58, (2003), pp. 347-352.
An article entitled "A Novel and Efficient Method for the . . . ", By Park et al., published by Bull. Chem. Soc. Jpn., vol. 76, (2003), pp. 1977-1981.
An article entitled "Understanding the Radiolabeling Mechanims . . . ", By Tsopelas, published by Applied Radiation and Isotopes, vol. 59, (2003), pp. 321-328.

* cited by examiner

*Primary Examiner*—John Pak
(74) *Attorney, Agent, or Firm*—Bachman & LaPointe, P.C.

(57) ABSTRACT

The present invention relates to a preparation method for technetium-antimony trisulfide nanocolloid, more precisely, a preparation method for technetium-antimony trisulfide nanocolloid which is characterized by the processes of mixing and stirring or irradiating of pertechnetate and antimony sulfide nanocolloid in the presence of borohydride exchange resin to obtain the technetium-antimony trisulfide nanocolloid radioactive complex.

7 Claims, 2 Drawing Sheets

【FIGURE. 1】
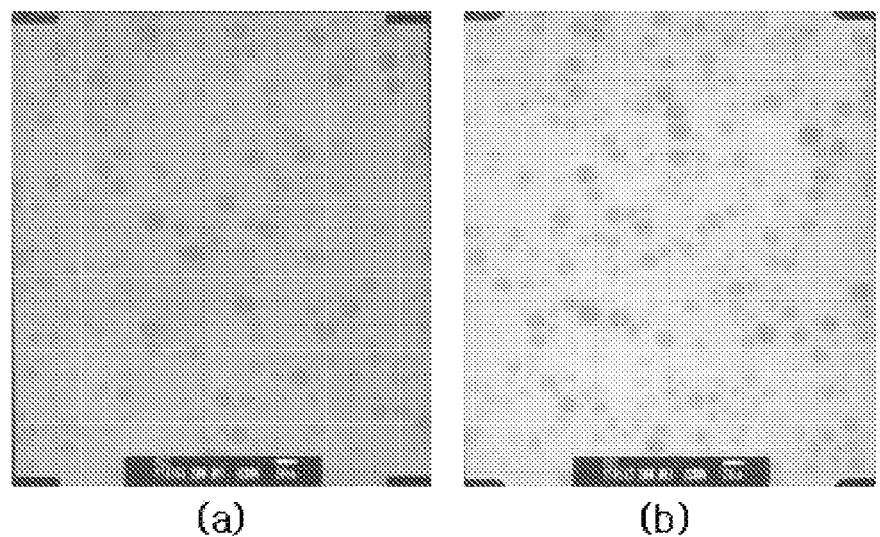
(a)　　　　　　　　(b)
【FIGURE. 2】
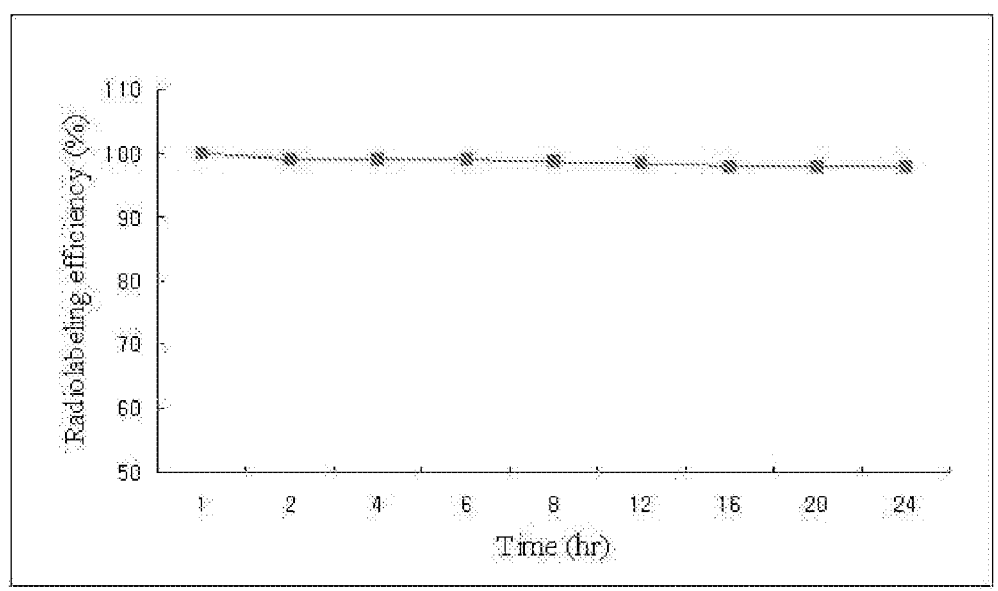

【FIGURE. 3】
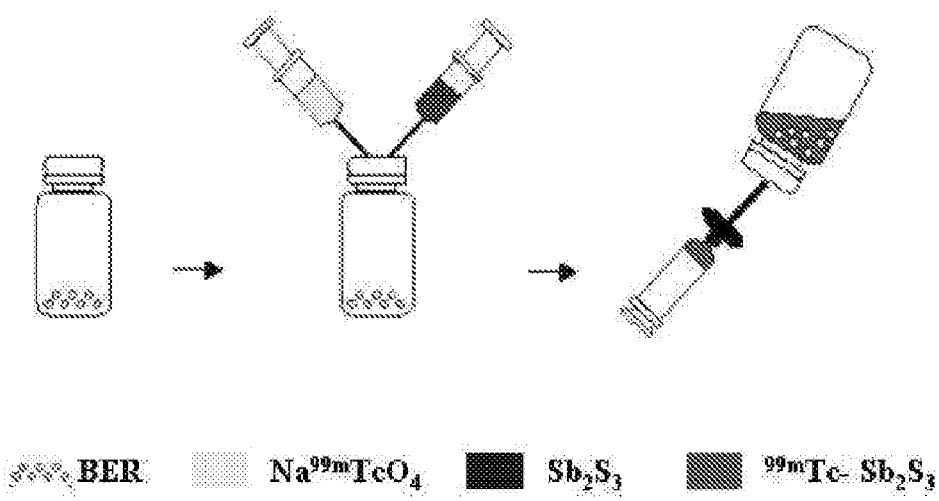

METHOD FOR PREPARING TECHNETIUM-LABELED ANTIMONY SULFIDE NANOCOLLOID

TECHNICAL FIELD

The present invention relates to a preparation method of technetium-antimony trisulfide nanocolloid, more precisely, a preparation method of technetium-antimony trisulfide nanocolloid using borohydride exchange resin (BER).

BACKGROUND ART

Technetium-99m ($^{99m}$Tc) is a kind of radionuclides which has been most widely used in diagnostic radiopharmaceuticals owing to its comparatively short half-life (6 hour) and gamma ray emission of 140 keV which is appropriate for obtaining a gamma image along with low prices and ready availability. The $^{99m}$Tc forms a complex by reacting with a compound having a lone electron pair such as isocyanate group, amine group, carboxyl group, thiol group, etc, which is used as an imaging agent or a labeling agent for various organs or tissues including lung, liver, brain, etc.

Reduction of technetium has to be performed prior to the reaction of pertechnetate and ligand to form a radioactive complex. At this time, reduction is performed by electrolysis or by a reducing agent such as $SnCl_2 \cdot 2H_2O$, $Fe^{++}$, ascorbate containing $Fe^{++}$, formamidinesulfinic acid, sodium borohydride, etc is used. Among those reducing agents, $SnCl_2 \cdot 2H_2O$ is most popular.

Among many $^{99m}$Tc complexes, $^{99m}$Tc—$Sb_2S_3$ nanocolloid (technetium-99m labeled antimony trisulfide nanocolloid, $^{99m}$Tc-ASC) has been widely used for lymphoscintigraphy or bone marrow scintigraphy.

The $^{99m}$Tc—$Sb_2S_3$ nanocolloid is formed by the reaction of pertechnetate and $Sb_2S_3$ nanocolloid in the presence of a reducing agent. As a reducing agent, $SnCl_2$, $NaBH_4$ or HCl can be used and actually HCl is preferred. $SnCl_2$ is the most popular reducing agent but has a problem of producing tin colloid during the preparation processes of $^{99m}$Tc—$Sb_2S_3$ nanocolloid. However, $NaBH_4$ has a problem that stability changes according to pH.

The $^{99m}$Tc—$Sb_2S_3$ nanocolloid has been prepared by the conventional method as follows. Freeze-dried $Sb_2S_3$ nanocolloid and $Na^{99m}TcO_4$ are mixed together in the presence of HCl, followed by heating for 30 minutes. Then, a buffer is added and pH is adjusted to 6-7. The size of the obtained $^{99m}$Tc—$Sb_2S_3$ nanocolloid particle is 5-20 nm (mostly 7-15 nm).

As explained above, the conventional preparation method for $^{99m}$Tc—$Sb_2S_3$ nanocolloid requires HCl as a reducing agent, and it has to be heated for reaction. Such reaction at high temperature brings difficulties in handling and often causes breakdown of chemical bond. Besides, pH has to be re-adjusted to neutral for the administration to a patient.

DISCLOSURE

Technical Problem

It is an object of the present invention to provide an easier and much economical preparation method for technetium-antimony trisulfide nanocolloid than the conventional method, in order to overcome the above problems, which is characterized by reaction at room temperature, deletion of pH regulating stage and shortening of reaction time.

Technical Solution

In order to achieve the above object, the present invention provides a preparation method of technetium-antimony trisulfide nanocolloid complex using borohydride exchange resin.

Hereinafter, the present invention is described in detail.

The present invention provides a preparation method for technetium-antimony trisulfide nanocolloid complex using borohydride exchange resin as a reducing agent, more precisely, a preparation method for technetium-antimony trisulfide nanocolloid complex by mixing a pertechnetate, antimony trisulfide nanocolloid and borohydride exchange resin to provide the mixture and then stirring the mixture.

The method of the present invention characteristically uses borohydride exchange resin as a reducing agent. The borohydride exchange resin has structure that borohydride ion ($BH_4^-$) binds to cation attached to macromolecule. $NH_4^+$ is used as a cation suitable for the fixation of borohydride ion. Every anion exchange resin having $NH_4^+$ (quaternary ammonium functionality) can be used as an exchange resin for the fixation of borohydride ion. Such exchange resin is easily obtainable and contains polystyrene, high density polyethylene, amberite, etc.

The borohydride exchange resin is very stable in either acidic or basic condition, so it is easily applied to biomolecules and also simply eliminated by filtering.

In the present invention, reaction is carried out at room temperature. Contrary to the conventional method for preparing technetium-antimony trisulfide nanocolloid complex performed at 100° C., the reaction is conducted at room temperature in the present invention, indicating that it can minimize problems such as troublesome operations at high temperature, instability of chemical bond, etc.

Pertechnetate of the present invention is formed by $^{99m}TcO_4^-$, more preferably by $Na^{99m}TcO_4$, and antimony trisulfide nanocolloid is prepared by the conventional method widely used in this field.

The present invention also provides a preparation method for technetitum-antimony trisulfide nanocolloid complex by mixing a pertechnetate antimony trisulfide nanocolloid and borohydride exchange resin, and then irradiating the mixture with microwave.

The final product is prepared by using the same starting material as described in the above method, and microwave irradiation is additionally performed after mixing. Microwave irradiation shortens reaction time. Precisely, reaction is completed within 1-2 minutes by microwave irradiation, which used to take 30 minutes with the conventional method, meaning that the preparation time for the administration to a patient is shortened.

There is no fixed order for adding to mix the starting materials in the present invention. Either simultaneous injection of pertechnetate and antimony trisulfide nanocolloid to borohydride exchange resin or sequential addition of the two to borohydride is possible. As shown in FIG. 3, it is preferred for the clinical use that pertechnetate and antimony trisulfide nanocolloid are added to vial containing borohydride exchange resin, followed by reaction at room temperature for a while, and then technetium-antimony trisulfide nanocolloid complex is obtained by using a syringe.

BRIEF DESCRIPTION OF THE DRAWINGS

FIG. 1 is a set of microphotograph showing TEM image of technetium-antimony trisulfide ($^{99m}$Tc—$Sb_2S_3$) nanocolloid, in particular, (a) shows $^{99m}$Tc—$Sb_2S_3$ nanocolloid prepared in comparative example 1, and (b) shows $^{99m}$Tc—Sb$_2$S$_3$ nanocolloid prepared in example 1, FIG. 2 is a graph showing the stability of technetium-antimony trisulfide ($^{99m}$Tc—Sb$_2$S$_3$) nanocolloid of the present invention, FIG. 3 is a schematic diagram showing an example of clinical application of the method of the present invention.

MODE FOR INVENTION

Practically preferred embodiments of the present invention are illustrative as shown in the following Examples.

However, it will be appreciated that those skilled in the art, on consideration of this disclosure, may make modifications and improvements within the spirit and scope of the present invention.

<PREPARATIVE EXAMPLE 1> Preparation of Antimony Trisulfide Nanocolloides (ASC, Sb$_2$S$_3$)

Hydrogen sulfide (H$_2$S) was added into 120 ml of distilled water that was cooled to 0~5° C., to prepare the saturated hydrogen sulfide solution. 10 ml of 3.5% polyvinylpyrrolidone (PVP-mw 40,000) was added into the saturated hydrogen sulfide solution. After stirring for 5 minutes, 20 ml of 1% antimony potassium tartrate was added, followed by further stirring for 5 minutes to give antimony trisulfide nanocolloid (Sb$_2$S$_3$ nanocolloid). Hydrogen sulfide was eliminated by using nitrogen gas, and the elimination of hydrogen sulfide was confirmed by lead acetate paper. The solution was filtered by 0.22 μm membrane filter, then sterilized and stored in a 0° C. refrigerator.

<EXAMPLE 1> Preparation of $^{99m}$Tc-ASC by the Method of the Present Invention 1.5 Ml of distilled water was added to the mixture of 1.2 mg of Sb$_2$S$_3$ nanocolloid, 5 mg of borohydride exchange resin and 1 Ml of Na$^{99m}$TcO$_4$ (40~50 mCi). The obtained solution was stirred at room temperature for 30 minutes until the reaction was completed. The resultant $^{99m}$Tc—Sb$_2$S$_3$ nanocolloid ($^{99m}$Tc-labeled antimony trisulfide nanocolloid) had a particle size ranging from 5 to 20 nm (mostly 7~15 nm) (see FIG. 1b).

Yield of the obtained $^{99m}$Tc—Sb$_2$S$_3$ nanocolloid was measured by ITLC (instant thin-layer chromatography). And the results are shown in Table 1.

TABLE 1

| Chromatography System | | Kinds of $^{99m}$Tc | |
|---|---|---|---|
| Supporter | Solvent | Origin | Solvent Front |
| ITLC-silica gel | Acetone | 100% $^{99m}$Tc—Sb$_2$S$_3$ | 0% $^{99m}$TcO$_4^-$ |
| ITLC-silica gel | Saline | 100% $^{99m}$Tc—Sb$_2$S$_3$ | 0% $^{99m}$TcO$_4^-$ |

As shown in Table 1, there was no observation of a peak of the first reactant at solvent front, but a peak of $^{99m}$Tc—Sb$_2$S$_3$ was observed. The results indicate that the complex is formed by the method of the present invention with over 99% yield.

<EXAMPLE 2> Preparation of $^{99m}$Tc-ASC by the Method of the Present Invention 1.5 Ml of distilled water was added to the mixture of 1.2 mg of Sb$_2$S$_3$ nanocolloid, 5 Mg of borohydride exchange resin and 1 Ml of Na$^{99m}$TcO$_4$ (40~50 mCi). The obtained solution was irradiated with microwave for 1-2 minutes until the reaction was completed. The resultant $^{99m}$Tc—Sb$_2$S$_3$ nanocolloid ($^{99m}$Tc-labeled antimony trisulfide nanocolloid) had a particle size ranging from 5 to 20 nm (mostly 7~15 nm) (FIG. 1b).

Yield of the obtained $^{99m}$Tc—Sb$_2$S$_3$ nanocolloid was measured by ITLC (instant thin-layer chromatography). And the results are shown in Table 2.

TABLE 2

| Chromatography System | | Kinds of $^{99m}$Tc | |
|---|---|---|---|
| Supporter | Solvent | Origin | Solvent front |
| ITLC-silica gel | Acetone | 100% $^{99m}$Tc—Sb$_2$S$_3$ | 0% $^{99m}$TcO$_4^-$ |
| ITLC-silica gel | Saline | 100% $^{99m}$Tc—Sb$_2$S$_3$ | 0% $^{99m}$TcO$_4^-$ |

As shown in Table 2, there was no observation of a peak of the first reactant at solvent front, but a peak of $^{99m}$Tc—Sb$_2$S$_3$ was observed. The results indicate that the complex is formed by the method of the present invention with over 99% yield.

<COMPARATIVE EXAMPLE 1> Preparation of $^{99m}$Tc-ASC by the Conventional Method 1.5 ml of distilled water was added to the mixture of 1.2 mg of Sb$_2$S$_3$ nanocolloid, 0.2 ml of 0.5 N HCL and 1 ml of Na$^{99m}$TcO$_4$. The solution was heated at 100° C. for 30 minutes, and then cooled at room temperature. At that time, pH was 1.5~1.8. 0.5 ml of sodium acetate buffer (0.35 M, pH 8) was added to adjust pH to 6.5. The resultant $^{99m}$Tc—Sb$_2$S$_3$ ($^{99m}$Tc-labeled antimony trisulfide nanocolloid) had a particle size ranging from 5 to 20 nm (mostly 7~15 nm) (see FIG. 1a).

<EXPERIMENTAL EXAMPLE 1> Stability of $^{99m}$Tc—Sb$_2$S$_3$ Nanocolloid of the Present Invention In order to investigate the stability of $^{99m}$Tc—Sb$_2$S$_3$ nanocolloid of the present invention, $^{99m}$Tc—Sb$_2$S$_3$ nanocolloid solution, prepared in the example 1, was stored in closed vacuum vials, which were left at room temperature for 1, 2, 4, 6, 8, 12, 16, 20, and 24 hours, respectively. The results are shown in FIG. 2.

As shown in FIG. 2, over 98% stability was not changed until 24 hours.

INDUSTRIAL APPLICABILITY

As explained hereinbefore, contrary to the conventional preparation method, the preparation method for technetium-antimony trisulfide nanocolloid complex of the present invention is characterized by using borohydride exchange resin as a reducing agent, conducting reaction at room temperature to provide technetium complex with high yield and shortening reaction time by omitting pH re-adjusting process. In addition, the reduction is achieved not in liquid but in solid phase, so a reducing agent can be easily eliminated by simple filtering regardless of its used amount. Thus, the preparation of the complex in the present invention is easier and much economical than the conventional method. Besides, reaction time is shortened by using microwave, meaning that preparation time for administration to a patient is much reduced.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for preparing technetium-antimony trisulfide nanocolloid complex, comprising mixing a pertechnetate, antimony trisulfide nanocolloid and a reducing agent to provide a mixture, and stirring the mixture to obtain said complex, wherein the reducing agent is borohydride exchange resin.

2. A method for preparing technetium-antimony trisulfide nanocolloid complex, comprising mixing a pertechnetate, antimony trisulfide nanocolloid, and a reducing agent to provide a mixture, and irradiating the mixture to obtain said complex, wherein the reducing agent is borohydride exchange resin.

3. A method as set forth in claim 2, wherein the mixture is irradiated with microwave for 1 to 2 minutes.

4. A method as set forth in claim 1 or claim 2, wherein the pertechnetate is $Na^{99m}TcO_4$.

5. A method as set forth in claim 1 or claim 2, wherein the method is carried out at room temperature.

6. A method as set forth in claim 1 or claim 2, wherein technetium-antimony trisulfide complex has a particle size ranging from 5 to 20 nm.

7. A method as set forth in claim 1, wherein the mixture of pertechnetate, antimony trisulfide and a reducing agent is stirred for 30 minutes.

* * * * *